United States Patent [19]

Ferrero

[11] Patent Number: 5,478,561
[45] Date of Patent: Dec. 26, 1995

[54] PROCESS FOR THE PREPARATION OF STABLE COMPLEX MULTIPLE EMULSIONS OF THE WATER-OIL WATER SYSTEMS

[75] Inventor: Louis Ferrero, Nice, France

[73] Assignee: Lancaster Group AG, Germany

[21] Appl. No.: 179,545

[22] Filed: Jan. 10, 1994

Related U.S. Application Data

[63] Continuation of Ser. No. 970,775, Nov. 3, 1992, abandoned.

[30] Foreign Application Priority Data

Nov. 7, 1991 [DE] Germany .......................... 41 36 699.9

[51] Int. Cl.$^6$ ....................................... A61K 7/00
[52] U.S. Cl. ........................... 424/401; 514/938; 514/939; 514/940; 514/941; 514/943
[58] Field of Search ................... 424/401; 514/938–943; 252/312

[56] References Cited

U.S. PATENT DOCUMENTS

| | | | |
|---|---|---|---|
| 4,714,566 | 12/1987 | Takahashi et al. | 252/314 |
| 4,985,250 | 1/1991 | Bee et al. | 424/401 |

FOREIGN PATENT DOCUMENTS

| | | |
|---|---|---|
| 0174377 | 3/1986 | European Pat. Off. . |
| 1541463 | 2/1979 | United Kingdom . |

OTHER PUBLICATIONS

Stabilization . . . Release, T. K. Law, *Journal of Controlled Release*, 3: 279–290 (1986), Elsevier Science Publishers B.V. Amsterdam.

Grant and Hack's Chemical dictionary p. 578, 1987.

*Primary Examiner*—Jyothsna Venkat
*Attorney, Agent, or Firm*—Rosenman & Colin

[57] ABSTRACT

The invention relates to a novel process for the preparation of stable complex multiple emulsions of the water-oil-water type which are well suited for use in cosmetic preparations. The primary emulsions of the W/O type are prepared in the presence of both a non-ionic polymeric lipophilic emulsifier and a non-ionic polymeric stabiliser each preferably having an HLB value in the range from 6 to 10. In a second process step more water containing a hydrophilic emulsifier having a higher HLB value, preferably in the range from 12 to 25, is added to the primary emulsion until phase inversion occurs. It is important that the procedure in this second process step is not reversed, i.e. that the primary emulsion is not added to the aqueous phase. Further active substances, such as UV filters and vitamins, may be added to the aqueous or oil phase respectively. In a third process step hydrating agents and/or gelling agents may be added, thus increasing the viscosity without impairing the stability of the multiple emulsion.

10 Claims, No Drawings

PROCESS FOR THE PREPARATION OF STABLE COMPLEX MULTIPLE EMULSIONS OF THE WATER-OIL WATER SYSTEMS

This is a continuation of Ser. No. 07/970,775, filed on Nov. 3, 1992, now abandoned.

The present invention relates to a novel process for the preparation of multiple emulsions of the water-oil-water (W/O/W) type, with the special aim of using such emulsions in cosmetic products.

The preparation of such emulsions is described in British Patent No. 1541463 (Lion Dentifrice Co.) and in an article by Florence and Whitehill with the title "The Formation and Stability of Multiple Emulsions" in the International Journal of Pharmaceutics II(1982) pp. 277–308. Further information can be obtained from a scientific lecture entitled "Les émulsions multiples", by M. Seiller et al., which was presented at the 2nd World Congress for Surface Active Materials—CESIO, held in Paris from 24–27 May 1988.

According to the said publications water/oil/water emulsions are produced by stirring an aqueous phase and an oil phase in the presence of a first surfactant with the formation of a water/oil/(water-in-oil) emulsion, and pouring the water/oil emulsion into an aqueous phase which contains a second surfactant, and by stirring the mixture to form the water/oil/water multiple emulsion. It is shown that the preparation of stable multiple emulsions represents a difficult problem.

The object of the invention was, therefore, to solve the problem of the preparation of such complex multiple emulsions which have sufficient stability for practical use.

Surprisingly it has been found that solving this problem requires the use of a combination of non-ionic emulsifier and non-ionic stabiliser in the composition of the primary emulsion (W/O), and that, in addition, the way in which this primary emulsion is combined with further amounts of an aqueous phase to bring about phase inversion is important.

The process according to the invention for the preparation of stable complex emulsion systems of the water-oil-water (W/O/W) type is thus characterised in that a) a primary emulsion of the W/O type is prepared at elevated temperature from a mineral oil and, if necessary, additionally a further oil component in the form of an ester of a fatty acid and/or in the form of a fatty alcohol, and water which, if necessary, contains a component having hydrating and/or gelling activity, and in the presence of a non-ionic polymeric lipophilic emulsifier and a non-ionic polymeric stabiliser, neither having an excessive HLB value, b) just enough water containing a hydrophilic emulsifier having a higher HLB value is added to this emulsion, slowly and with stirring without generating shear forces, at ambient temperature, so that phase inversion occurs, the components having hydrating and/or gelling activity which were added if necessary in step (a) being included in the inner aqueous phase of the W/O/W emulsion, and, if necessary, c) a component having hydrating and/or gelling activity is incorporated into the complex W/O/W emulsion thus formed, with gentle stirring at ambient temperature, Step (b) is fundamental since this reversal of the addition of the primary emulsion and water, compared with the previous method of working, makes it possible for the first time to prepare truly stable multiple emulsions, as will be further explained below by means of examples and experiments.

The formation of the desired multiple emulsion can be ascertained by monitoring the process by means of conductivity measurement until the emulsion inversion point has been reached.

The advantage of the reversed addition method, in addition to the stability of the W/O/W emulsions, resides in the fact that only one emulsifying mixer is required for the preparation of the multiple emulsion.

The measure of adding thickeners or gelling agents in step (a) or the corresponding concluding measure according to step (c) allows the viscosity of the multiple emulsion to be modified, which is of importance for the use as a cosmetic preparation, for example in the form of a liquid milk or a cream.

As a further oil component in step (a) it is expedient to use a vegetable oil, in particular oil of borage. Oil of borage contains triglycerides of γ-linolenic acid and is obtained from the seed of the borage plant.

However, other oils such as animal oils may also be employed.

Process step (a) is expediently carried out at elevated temperature up to 70° C. in order to ensure good mixing of all solid and/or liquid components.

The lipophilic emulsifier employed in process step (a) preferably has an HLB (hydrophilic lipophilic balance) value in the range from 6 to 10.

Especially suitable for this purpose is a methoxypolyethylene glycol-dodecyl glycol copolymer, for example a commercially available polymeric product of the methoxypolyethylene glycol(22)-dodecyl glycol type, which corresponds to the following formula:

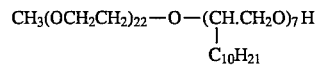

Such a copolymer has, for example, an average molecular weight of approximately 1,800.

The stabiliser co-used in process step (a) is also a polymeric product whose HLB value is likewise expediently in the range from 6 to 10. Very suitable for this purpose are copolymers of the same type as the emulsifier, for example a polyethylene glycol-dodecyl glycol copolymer. A commercial product with an average molecular weight in the range from 2,300 to 4,000 may suitably be employed, for example a polymer with the following formula

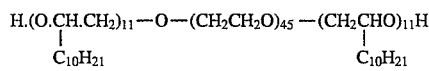

In process step (b), a hydrophilic emulsifier is also used, in the aqueous phase, which expediently has an HLB value in the range from 12 to 25 and in particular from 15 to 22. Very suitable for this purpose are commercially available ethylene oxide-propylene oxide block copolymers with average molecular weights of between 10,000 and 15,000, for example a copolymer with the following formula

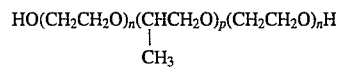

Another suitable commercial product is a methoxypolyethylene glycol(17)-dodecyl glycol copolymer with an HLB value of 15.

It is possible to add one or more oil-soluble active components, such as unsaponifiable components of vegetable oils, for example of Zea Mays, vitamins, for example dl-α-tocopherol acetate, and UV filters such as octyl methoxycinnamate, to the oil phase before or after the formation of the primary emulsion in process step(a).

The water-in-oil emulsion can, in addition, contain hydrating or gelling agents, such as polyglyceryl methacrylate and propylene glycol (commercial product LUBRAJEL CG), sodium hyaluronate gel or Aloe vera gel. It can further contain cerebrosides, cholesterol or phospholipids, which may function as additional stabilisers.

Viscosity modifiers or gelling agents for the multiple emulsion which may be mentioned are polyglyceryl methacrylate and xanthan gum.

A multiple emulsion produced according to the invention using the substances mentioned feels particularly pleasant when spread on the skin.

The following examples serve to illustrate the advantage of the process according to the invention:

EXAMPLE 1

Composition of the primary emulsion (%)

|  | Emulsion 1 | Emulsion 2 | Emulsion 3 | Emulsion 4 |
|---|---|---|---|---|
| Mineral oil | 26 | 26 | 26 | 26 |
| Elfacos(R) E 200x) (emulsifier) | 4 | 0 | 2 | 1 |
| Elfacos(R) ST9xx) (stabiliser) | 0 | 4 | 2 | 3 |
| H$_2$O | 66 | 66 | 66 | 66 |
| NaCl | 4 | 4 | 4 | 4 | x)Commercially available non-ionic polymeric emulsifier of the methoxypolyethylene glycol(22) dodecyl glycol copolymer type (HLB value approx. 8.5)
xx)Commercially available non-ionic polymeric stabiliser of the polyethylene glycol(45)-dodecyl glycol copolymer type with an HLB value of 6.5.

Procedure: for 300 g of primary emulsion: the oil phase, composed of mineral oil, emulsifier and stabiliser, is warmed to 70° C. Sodium chloride and water are heated to 70° C. This aqueous phase is added, for the purpose of obtaining a W/O emulsion, to the oil phase, which is stirred at high speed with a homogenising mixer until it has cooled to room temperature.

| Composition of the aqueous phase (%) | |
|---|---|
| Synperonic(R) PE/F 127* | 5 |
| Water | 94.6 |
| Glydant** | 0.4 |

*Commercially available hydrophilic emulsifier in the form of an ethylene oxide-propylene oxide block copolymer with a high MW (approx. 12,000) and a HLB value of 22.
**A preservative employed in cosmetic products.

Procedure: These substances are dissolved in water at room temperature with stirring without generating shear forces.

Inversion of the primary emulsion

Procedure: The aqueous phase is slowly added to the primary emulsion, with gentle stirring, at room temperature.

The phase inversion becomes visible to the eye. It is checked by means of a conductivity meter. The following composition of the final emulsion in % is obtained after the phase inversion:

|  | Emulsion 1 | Emulsion 2 | Emulsion 3 | Emulsion 4 |
|---|---|---|---|---|
| % primary emulsion | 95 | 80 | 87 | 83 |
| % aqueous phase | 5 | 20 | 13 | 17 |
| Viscosity after 3 months, cps | 5661 | 7492 | 7326 | 11,600 |
| Conductivity after 3 months, mS/cm | 2.82 | 1.59 | 1.72 | 1.32 |
| Structure of this emulsion | multiple W/O/W | the same with large beads | the same | the same |
| Stability of this emulsion after 1 year | poor demulsification | good | good | good |

The W/O/W structure is confirmed by examination under a microscope.

Note: The main effect of the co-use of Elfacos® ST9 (stabiliser for the W/O primary emulsion) is to so increase the content of aqueous phase that enough water is present to reach the phase inversion point. The multiple emulsion obtained is more stable in the presence of the stabiliser.

EXAMPLE 2

Structure of the primary emulsion: see emulsion 4.
Structure of the aqueous phase: as previously described.
Inversion of the primary emulsion
The following results are obtained:

|  | Experiment 1 | Experiment 2 | Experiment 3 |
|---|---|---|---|
| Conditions for phase inversion | Addition of aqueous phase stopped immediately after inversion | Excess aqueous phase after inversion | Large excess after inversion |
| % primary emulsion | 82 | 73 | 64 |
| % aqueous phase | 18 | 27 | 36 |
| Viscosity after 3 months, cps | 10,000 | 7,000 | 4,000 |
| Conductivity after 3 months, mS/cm | 1.45 | 2.42 | 4.29 |
| Structure of this emulsion | Multiple W/O/W emulsion | the same | not clear |
| Stability of the emulsion | good | demulsification | extensive demulsification |

Note: The best W/O/W stability is obtained if the addition of aqueous phase is stopped immediately after the phase inversion.

For the remaining examples the composition of the aqueous phase is modified: Lubrajel® CG (polyglyceryl methacrylate and propylene glycol) as a component with hydrating and gelling activity was added to the inner aqueous phase of the primary emulsion. Due to incompatibility with this gelling agent, sodium chloride must be omitted.

EXAMPLE 3

Composition of the Primary Emulsion (%)

|  | Emulsion 5 | Emulsion 6 |
|---|---|---|
| Mineral oil | 26 | 16 |
| Oil of borage | 0 | 4 |
| Octyl methoxycinnamate | 0 | 4 |
| Elfacos(R) E200 | 1 | 1 |
| Elfacos(R) ST9 | 3 | 3 |
| $H_2O$ | 59.5 | 59.5 |
| Lubrajel(R) CG | 10 | 10 |
| DL-α-tocopherol acetate | 0 | 2 |
| Phenonip* | 0.5 | 0.5 |

*Preservative used in cosmetic products: phenoxyethanol and (methyl-ethyl-propyl-butyl)paraben.

Procedure: For 300 g of primary emulsion, as described above for the procedure in Example 1, with the exception of the addition of DL-e-tocopherol acetate, which is added after the emulsification, at 40° C. The Lubrajel® CG is dissolved in the aqueous phase in advance.

Composition of the aqueous phase: as described in Example 1.

Evaluation of the results of the preparation of multiple emulsions.

2 Methods are used:

1. The technique of dispersion of the W/O primary emulsion in the aqueous phase by the procedure described by Seiller (loc.cit.). The addition of the primary emulsion is stopped after the thickening of the dispersion.

2. The technique according to the invention, as described above in Examples 1 and 2: phase inversion in 2 steps.

borage, octyl methoxycinnamate and DL-α-tocopherol acetate as polar components.

EXAMPLE 4

Co-use of further active components in the primary emulsion.

Composition of the primary emulsion (%)

|  | Emulsion 7 | Emulsion 8 | Emulsion 9 | Emulsion 10 |
|---|---|---|---|---|
| Mineral oil | 15.9 | 15.5 | 14.9 | 14.9 |
| Oil of borage | 4 | 4 | 4 | 4 |
| Octyl methoxy-cinnamate | 4 | 4 | 4 | 4 |
| Cholesterol | 0.1 | 0 | 0.1 | 0.1 |
| Unsaponifiable substance from Zea Mays | 0 | 0.5 | 0.5 | 0.5 |
| Ceramide(x) | 0 | 0 | 0.5 | 0.5 |
| Elfacos(R) E200 | 1 | 1 | 1 | 1 |
| Elfacos(R) ST9 | 3 | 3 | 3 | 1.5 |
| Water | 59.5 | 59.5 | 59.5 | 61 |
| Lubrajel CG | 10 | 10 | 10 | 10 |
| Tocopherol acetate | 2 | 2 | 2 | 2 |
| Phenonip | 0.5 | 0.5 | 0.5 | 0.5 | x)This complex additive consists of a mixture of glycosphingolipids, phospholipids and cholesterol.
Procedure: the same procedure as in Example 3.
Composition of the aqueous phase: as in Example 1.

Conversion of the W/O primary emulsion into a complex emulsion by phase inversion.

The following results are obtained:

|  | Emulsion 7 | Emulsion 8 | Emulsion 9 | Emulsion 10 |
|---|---|---|---|---|
| % primary emulsion | 60 | 66 | 33 | 67 |

|  | Emulsion 5 | | Emulsion 6E | |
|---|---|---|---|---|
| Technique for the inversion of W/O | Phase inversion | W/O Dispersion | Phase inversion | W/O Dispersion |
| % Primary emulsion | 86 | 85 | 59 | 75 |
| % Aqueous phase | 14 | 15 | 41 | 25 |
| Viscosity after 3 months, cps | liquid | liquid | 11,200 | liquid |
| Conductivity after 3 months, μS/cm | 35 | 30 | 16 | 20 |
| Structure of the emulsion | not multiple, simple beads | not multiple, simple beads W/O/W | multiple | not multiple, simple beads |
| Stability of the emulsion after 3 months | demulsification | demulsification | good | demulsification |

Note: In the case of Emulsion No. 5 it is not possible to obtain a multiple emulsion with Lubrajel CG and without sodium chloride. In contrast to this, in Emulsion No. 6, the co-use of oily components which contain polar groups makes it possible to prepare a complex emulsion after the phase inversion process. Emulsion No. 6 contains oil of -continued

|  | Emulsion 7 | Emulsion 8 | Emulsion 9 | Emulsion 10 |
|---|---|---|---|---|
| % aqueous | 40 | 34 | 67 | 33 |

-continued

|  | Emulsion 7 | Emulsion 8 | Emulsion 9 | Emulsion 10 |
|---|---|---|---|---|
| phase |  |  |  |  |
| Viscosity after 3 months, cps | 25,200 | 21,000 | 12,000 | 15,000 |
| Conductivity after 3 months, µS/cm | 5.8 | 8.0 | 5.0 | 18 |
| Structure of the emulsion | multiple W/O/W | multiple W/O/W | multiple but hardly dispersible in water | multiple W/O/W |
| Stability of the emulsion after 3 months | good | good | good | good |

Cholesterol and the unsaponifiable substance from Zea Mays have no significant effect on the volume fraction of the aqueous phase which is necessary (at the concentrations under investigation) in order for the phase inversion point to be reached.

This does not apply to ceramides, which increase this volume considerably. It can be assumed that this material acts as a lipophilic emulsifier (see Emulsion 9).

By virtue of the fact that it is possible to influence the stabiliser concentration (Elfacos® ST9: reduction from 3% to 1.5%), a good W/O/W emulsion may be obtained with a normal aqueous phase content (see emulsion 10).

EXAMPLE 5

W/O/W multiple emulsion gelling according to process step (c)

Composition of the primary emulsion: see Emulsion 10 in Example 4.

Conversion of this W/O primary emulsion into the complex emulsion by phase inversion: see the results previously obtained with the emulsion in Example 4.

Final gelling of multiple emulsion 10: Proportion of W/O/W emulsion 10: 95% Amount of Lubrajel® CG: 5%

Lubrajel® CG is added slowly with stirring, avoiding the generation of shear forces, to the complex multiple emulsion until completely dispersed.

At first the viscosity drops, but after standing for 24 hours the emulsion appears to be well gelled and remains in this state, as can be seen from the Table.

|  | Emulsion 10 before gelling | Emulsion 10 after gelling |
|---|---|---|
| Viscosity after 3 months, cps | 15,000 | 28,400 |
| Conductivity after 3 months µS/cm | 18 | 15 |
| Structure of the emulsion (under the microscope) | multiple W/O/W | multiple W/O/W |
| Stability of the emulsion after 3 months | good | good |

By the addition of perfume substances and, if necessary, further active substances which are customary in cosmetics, cosmetic preparations which can be thickened to any desired consistency may be produced from the stable multiple emulsions prepared according to the invention. As a result of their favourable thixotropic properties they are easily spread on, and well tolerated by, the skin. After gelling, emulsion No. 10 has excellent cosmetic properties and effects enduring moisture retention on the skin.

I claim:

1. A process for the preparation of stable complex W/O/W emulsion systems comprising:

a) preparing a primary W/O emulsion at an elevated temperature up to 70° C. from a mineral oil, water, and optionally at least one additional oil component selected from the group consisting of an ester of fatty acid and a fatty alcohol, wherein said water optionally containing a component having one of hydrating and gelling activity, said primary W/O emulsion being prepared in the presence of a non-ionic polymeric lipophilic emulsifier having an HLB value of 6 to 10, which is a methoxypolyethylene glycol (22) dodecyl glycol copolymer, and a non-ionic polymeric stabilizer, having an HLB value of 6 to 10, which is a polyethylene glycol (45)-dodecyl glycol copolymer;

b) adding water containing a hydrophilic emulsifier having an HLB value of 12 to 25, to said emulsion, slowly and with stirring without generating shear forces at room temperature so that phase inversion occurs, wherein said emulsifier is an ethylene oxide-propylene oxide block copolymer with an average molecular weight of 10,000 to 15,000, or methoxy PEG-17/dodecyl glycol copolymer; said component having one of hydrating and gelling activity which were added optionally in step (a) being included in the inner aqueous phase of the W/O/W emulsion; and c) optionally incorporating a component having one of hydrating and gelling activity into said stable complex W/O/W emulsion thus formed, with gentle stirring at room temperature.

2. The process according to claim 1, wherein said additional oil component selected from the group consisting of an ester of fatty acid and a fatty alcohol, used in step (a) is a vegetable oil.

3. The process according to claim 2, wherein said vegetable oil is oil of borage.

4. The process according to claim 1, wherein said additional oil component selected from the group consisting of an ester of fatty acid and a fatty alcohol, used in step (a) is an animal oil.

5. The process according to claim 1, wherein said non-ionic polymeric lipophilic emulsifier has an average molecular weight of 1,800.

6. The process according to claim 1, wherein said non-ionic polymeric stabilizer has an average molecular weight in the range from 2,300 to 4,000.

7. The process according to claim 1, which further comprises adding at least one oil-soluble active component selected from the group consisting of compounds acting as UV filters and vitamins to the oil phase before carrying out steps (a) and (b) or after step (b) has been completed.

8. The process according to claim 7, wherein said compound acting as a UV filter is octyl methoxy-cinnamate.

9. The process according to claim 1, wherein said components having hydrating and gelling activity which are used in the aqueous phase in step (a) and step (c) are propylene glycol and polyglyceryl methacrylate.

10. The process according to claim 9, wherein said vitamin is dl-α-tocopherol acetate.

* * * * *